US00PP26168P2

(12) United States Plant Patent
Kordes

(10) Patent No.: US PP26,168 P2
(45) Date of Patent: Dec. 1, 2015

(54) MINIATURE ROSE PLANT NAMED 'KORPOT009'

(50) Latin Name: *Rosa hybrida*
Varietal Denomination: KORpot009

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohns Rosenschulen GmbH & Co KG, Offenseth-Sparrieshoop (DE)

( * ) Notice: Subject to any disclaimer, the term of this patent is extended or adjusted under 35 U.S.C. 154(b) by 54 days.

(21) Appl. No.: 13/987,161

(22) Filed: Jul. 3, 2013

(51) Int. Cl.
*A01H 5/02* (2006.01)

(52) U.S. Cl.
USPC ..... Plt./121

(58) Field of Classification Search
USPC ..... Plt./121
CPC ..... A01H 5/0222
See application file for complete search history.

*Primary Examiner* — Keith O. Robinson

(57) ABSTRACT

A new and distinct variety of rose with long lasting, novel deep pink flowers, and attractive foliage with very good disease resistance. It exhibits compact and bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot009'.

CROSS REFERENCES AND FEDERAL R&D STATEMENT

There are no cross referenced or related applications. This variety was developed without the aid of any research grant.

BACKGROUND OF THE INVENTION

The present discovery constitutes a new and distinct variety of a miniature pot rose plant which was discovered in a cultivated area in my nursery in July, 2011. The new rose variety resulted from a naturally occurring mutation of unknown causation on a branch of 'KORdatiffi', a non-patented rose by the same inventor.

The new rose plant was selected as a single plant due to its superior characteristics and asexually propagated for further evaluation. This new and distinctive rose variety is named 'KORpot009'.

SUMMARY OF THE INVENTION

The new rose plant may be distinguished from its parent variety, 'KORdatiffi', by the following combination of characteristics:

1. The petal count of 'KORpot009' is very double with an average of 55 to 60 petals per flower, whereas the petal count of 'KORdatiffi' is double with an average of 30 to 40 petals per flower.
2. The general tonality on the open flowers of 'KORpot009' is Red-Purple Group 68A, while the general tonality on the open flowers of 'KORdatiffi' is Red Group 62B.

3. The average flower diameter of an open flower of 'KORpot009' is 60 to 65 mm, while the average flower diameter of an open flower of 'KORdatiffi' is 40 to 60 mm.

The objective of the selection was to develop a new and distinct rose plant with unique qualities, such as:

1. Compact and uniform growth and flowering under greenhouse conditions when grown as a potted floral plant;
2. Abundant, long lasting, and attractive dark pink flowers and foliage;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORpot009' from all other varieties of which I am aware.

As part of a rose development program, Tim-Hermann Kordes conducted evaluations and observations on the mutation in a controlled environment in Offenseth-Sparrieshoop, Germany. The new rose plant 'KORpot009' was selected in July 2011 to be asexually propagated for further evaluation. The first asexual propagation of 'KORpot009' was done by rooting softwood cuttings in July 2011 at the inventor's nursery in Offenseth-Sparrieshoop, Germany.

These initial and other subsequent propagations conducted in controlled environments demonstrate that 'KORpot009' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot009'.

DETAILED BOTANICAL DESCRIPTION

The following is a description of 'KORpot009', as observed growing in May 2013 in a nursery in Jackson County, Oreg. on plants of 6 months of age. Color references are made using The Royal Horticultural Society (London, England) Colour Chart, 2001 except where common terms of color are used.

For a comparison, several physical characteristics of the rose variety 'KORbalrom', a rose variety from the same inventor described and illustrated in U.S. Plant Pat. No. 19,025 and issued on Jul. 15, 2008 are compared to 'KORpot009' in Chart 1.

CHART 1

| Characteristic | 'KORpot009' | 'KORbalrom' |
|---|---|---|
| Foliage | Semi-glossy | Very glossy |
| Bud form | Short; pointed ovoid | Medium; globular |
| Number of leaflets per leaf | 5-7 | 5 |

Parent: 'KORdatiffi'.

Classification:

*Botanical classification.*—*Rosa hybrida* 'KORpot009'.

*Commercial classification.*—Miniature rose.

FLOWER AND FLOWER BUD

Blooming habit: Continuous.

Flower bud:

*Size.*—Upon opening, 25-30 mm in length from base of receptacle to distal end of bud and 15-20 mm diameter at its widest point.

*Bud form.*—Short. Pointed ovoid.

*Bud color.*—As sepals first unfold, bud color is Red-Purple Group N66A. When ¼ open, the upper surface of petals is Red-Purple Group 68A, and the lower surface is Red-Purple Group 67B.

*Sepals.*—Color: Upper surface: Green Group 138B. Lower surface: Green Group 138A. Size: Average 35 mm (l)×12 mm (w). Shape: Weak foliaceous appendages on 3 of the five sepals. Apex: Cirrose. Base: Flat at union with receptacle. Quantity: Five. Surface texture: Upper side: Moderately pubescent. Lower surface: Smooth, slightly pubescent. Margins: Pubescent with very limited stipitate glands.

Flower bloom:

*Fragrance.*—Very light.

*Duration.*—On the plant 14-18 days.

*Size.*—Medium for a miniature rose. When open, the average flower diameter is 60-65 mm and the average flower height is 35-40 mm.

*Shape.*—Open cup. Shape of the flower when viewed from the side: Upon opening, upper part: Convex. Upon opening, lower part: Convex. Open flower, upper part: Flat. Open flower, lower part: Concave.

Color:

*Upon opening, petals.*—Outermost petals: Outer Side: Red-Purple Group 67C. Inner Side: Red-Purple Group 68A. Innermost petals: Outer Side: Red Group 54A. Inner Side: Red Group 54B.

*Upon opening, basal petal spots.*—Basal petal spot, outermost petals: Outer Side: Yellow Group 2C. Inner Side: Yellow Group 2C. Basal petal spot, innermost petals: Outer Side: Yellow Group 3A. Inner Side: Yellow Group 2A.

*After opening, petals.*—Outermost petals: Outer Side: Red-Purple Group 67B. Inner Side: Red-Purple Group 68A. Some with center stripe Green White Group 157B. Innermost petals: Outer Side: Red Group 54B. Inner Side: Red Group 55A.

*After opening, basal petal spots.*—Basal petal spot, outermost petals: Outer Side: White Group 155C. Inner Side: White Group 155C. Basal petal spot, innermost petals: Outer Side: Yellow Group 2C. Inner Side: Yellow Group 2B.

General tonality: On open flower Red-Purple Group 68A. No change in the general tonality at the end of 8-10 days. Afterwards, general tonality is Red-Purple Group 68B.

Petals:

*Petal count.*—Very Double. Approximately 55-60 petals under normal conditions.

*Petal reflex.*—Petals reflex somewhat. Petal reflex occurs one at a time beginning with outermost petals.

*Petal margin.*—Entire to slightly undulated.

*Petal shape.*—Obovate to round. Apex: Obtuse. Base: Attenuate to obtuse.

*Petal size.*—20-26 mm (l)×22-30 mm (w). Size of the Basal Spot: 3-7 mm (l)×5-9 mm (w).

*Thickness.*—Average.

*Petal arrangement.*—Not formal.

*Texture.*—Outer Side: Smooth. Inner Side: Smooth.

Petaloids:

*Petaloid count.*—Average of 10-12 per flower.

*Petaloid size.*—10-14 mm (l)×8-10 mm (w).

*Petaloid color.*—Inner side: Red Group 45C. Outer side: Red Group 45B.

*Petaloid texture.*—Smooth.

*Margins.*—Entire to undulated.

*Petaloid shape.*—Most commonly obovate to spatulate. Apex: Obtuse. Base: Cuneate to attenuate.

Reproductive organs:

*Pistils.*—Abundant. Approximately 140-150 present. Stigmas: Location: Slightly inferior in position to anthers. Color: Greyed-Yellow Group 160D. Styles: Length: About 8 mm long. Color: Green White Group 157C. Intonations of Greyed- Purple Group 184D.

*Stamens.*—Approximately 140-150 on average and regularly arranged. Anthers: Size: Average 2.5 mm (l)×1.5 mm (w). Color: Greyed-Yellow Group 162B. Pollen: Generally absent. Filaments: Color: Yellow-Orange Group 15B. Length: Average 8-10 mm.

*Receptacle.*—Color: Yellow-Green Group 144A. Shape: Funnel-shaped. Texture: Smooth. Size: 10 mm (h)×15 mm (w).

*Pedicel.*—Length: 40-50 mm average length. Diameter: 2-3 mm average diameter. Color: Yellow-Green Group 144B. Strength: Somewhat strong. Texture: Smooth. Borne: Multiple flowers per flower shoot, generally 6 to 8. Flowers held upright.

*Peduncle.*—Length: 50-70 mm average length. Diameter: 3.5-4 mm average diameter. Color: Yellow-Green Group 144B. Strength: Strong. Texture: Smooth.

THE PLANT

Growth: Moderately vigorous.

Plant habit: Compact. When grown as a 10.5 cm pot plant, the average plant height is 25-30 cm and the average plant width is 15-20 cm.

Stems:

*Length*.—100-200 mm average length.

*Diameter*.—3-5 mm average diameter.

*Stem color*.—Young wood: Yellow-Green Group 146C. Older wood: Green Group 137C.

*Intonations*.—Greyed-Orange Group 167D on juvenile stems.

*Stem surface texture*.—Young wood: Smooth. Older wood: Smooth. Below initiation of inflorescence, laterals are non-flowering.

Prickles: Present.

*Incidence*.—Variable. Range from 2-3 prickles per 10 cm length of stem to 10-12 prickles per 10 cm length of stem.

*Size*.—Variable. On smaller stems 4-5 mm (l), on larger stems 5-8 mm (l).

*Color*.—Immature prickles: Greyed-Red Group 182B. Mature prickles: Greyed-Red Group 182D. Senescing to Greyed-Red Group 179D.

*Shape*.—Linear to concave.

*Anthocyanin*.—Greyed-Red Group 182A.

Leaves: Normally 5-7 leaflets on normal leaves in middle of the stem.

*Venation pattern*.—Pyramidal net pattern.

*Leaf size*.—100-120 mm (l)×60-70 mm (w).

*Abundance*.—Above average.

Leaflets:

*Size*.—Average size of the terminal leaflet is 32-36 mm (l)×24-26 mm (w).

*Shape*.—Ovate. Base: Obtuse. Apex: Acute.

*Margins*.—Finely serrated.

*Texture*.—Upper side of leaflet: Semi-glossy. Smooth. Under side of leaflet: Matte. Slightly rough.

*Color, mature foliage*.—Upper Leaflet Surface: Green Group 137A. Lower Leaflet Surface: Yellow-Green Group 147C.

*Color, juvenile foliage*.—Upper Leaflet Surface: Yellow-Green Group 146B. Lower Leaflet Surface: Yellow-Green Group 146C.

*Anthocyanin intonation*.—Greyed-Red Group 182B and Greyed-Red Group 182D. Location: Immature leaflets, stipules, petioles and petiole rachis.

*Arrangement*.—Odd pinnate.

*Venation*.—Reticulate.

Stipules:

*Size*.—12 mm (l)×5 mm (w).

*Stipule color*.—Green Group 137B.

*Anthocyanin*.—Greyed-Red Group 182B and Greyed-Red Group 182D.

*Margins*.—Finely serrated with moderate numbers of stipitate glands present.

*Texture*.—Smooth.

*Shape*.—Apex: Apiculate. Base: Flat.

Petiole:

*Length*.—Average 20 mm.

*Diameter*.—Average 1 mm.

*Petiole color*.—Green Group 137B. Underneath: Green Group 137B.

*Margins*.—With a few stipitate glands and white hairs.

*Anthocyanin*.—Greyed-Red Group 182B.

*Prickles*.—A few small prickles underneath.

*Stipitate glands*.—Limited.

*Texture*.—Nearly smooth.

Petiole rachis:

*Length*.—Average 15 mm.

*Diameter*.—Average 1 mm.

*Color*.—Green Group 137B. Anthocyanin present on juvenile tissue: Greyed-Red Group 182B.

*Margins*.—With a few stipitate glands and white hairs.

*Prickles*.—A few small prickles underneath.

Hips/seed formation: None observed.

Winter hardiness: To date, the variety has been grown successfully in Zone 7.

Disease resistance: Very good resistance to Powdery mildew (*Sphaerotheca pannosa*) and *Botrytis* (*Botrytis cinerea*) diseases under normal growing conditions in Jackson County, Oreg.

I claim:

1. A new and distinct variety of rose plant, as described and illustrated herein.

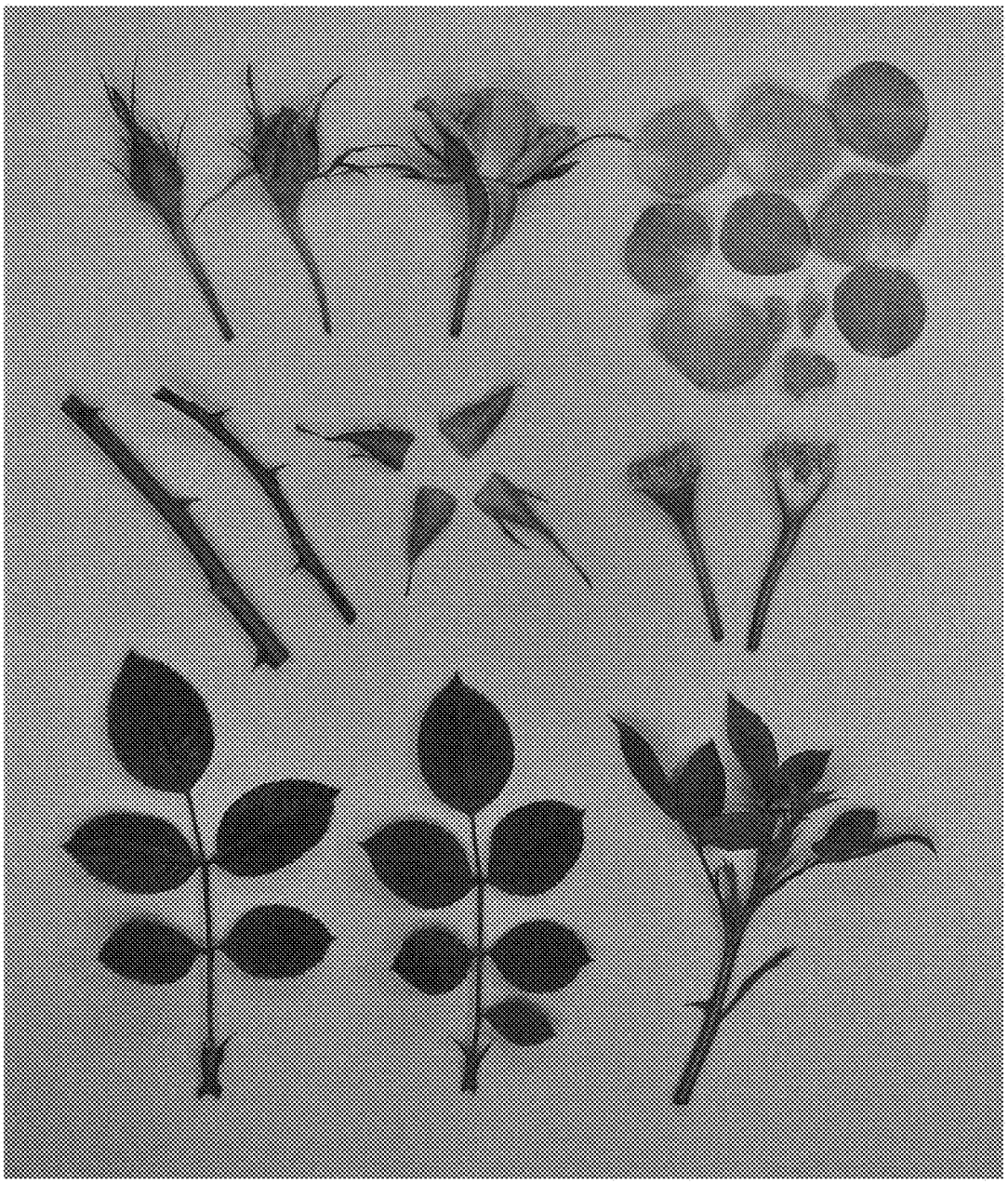

* * * * *